United States Patent [19]
Reiss et al.

[11] 4,093,668
[45] June 6, 1978

[54] MANUFACTURE OF BUTYNEDIOL

[75] Inventors: Wolfgang Reiss, Ludwigshafen; Hans-Ingo Joschek, Mannheim; Rudolf Schnur, Frankenthal; Siegfried Winderl, Heidelberg-Wieblingen; Juergen Dehler, Ludwigshafen; Herwig Hoffmann, Frankenthal, all of Germany

[73] Assignee: BASF Aktiengesellschaft, Ludwigshafen am Rhein, Germany

[21] Appl. No.: 452,565

[22] Filed: Mar. 19, 1974

[30] Foreign Application Priority Data
Mar. 24, 1973 Germany .............................. 2314693

[51] Int. Cl.$^2$ ............................................. C07C 29/00
[52] U.S. Cl. .................................................. 568/855
[58] Field of Search ........................ 260/635 Y, 632 Y

[56] References Cited
U.S. PATENT DOCUMENTS

| | | | |
|---|---|---|---|
| 2,300,969 | 11/1942 | Reppe et al. ...................... | 260/632 Y |
| 2,712,560 | 7/1955 | McKinley et al. ................ | 260/635 Y |
| 2,987,465 | 6/1961 | Johanson .............................. | 423/415 |
| 3,723,545 | 3/1973 | Nagel et al. ....................... | 260/635 Y |
| 3,781,373 | 12/1973 | Gobron et al. .................... | 260/635 C |

FOREIGN PATENT DOCUMENTS 698,019  10/1953  United Kingdom ............. 260/635 Y

OTHER PUBLICATIONS

Lange "Handbook of Chemistry", 10th ed. (1961), pp. 910–912.

Primary Examiner—Joseph E. Evans
Attorney, Agent, or Firm—Johnston, Keil, Thompson & Shurtleff

[57] ABSTRACT

Butynediol is prepared by reacting acetylene and formaldehyde in contact with a heavy metal acetylide as catalyst, in the liquid phase by the Reppe method. Acetylene is fed upwardly through a suspension of the catalyst in formaldehyde at such a rate that it is virtually completely consumed and a liquid zone containing no catalyst is formed above the suspension.

4 Claims, 1 Drawing Figure

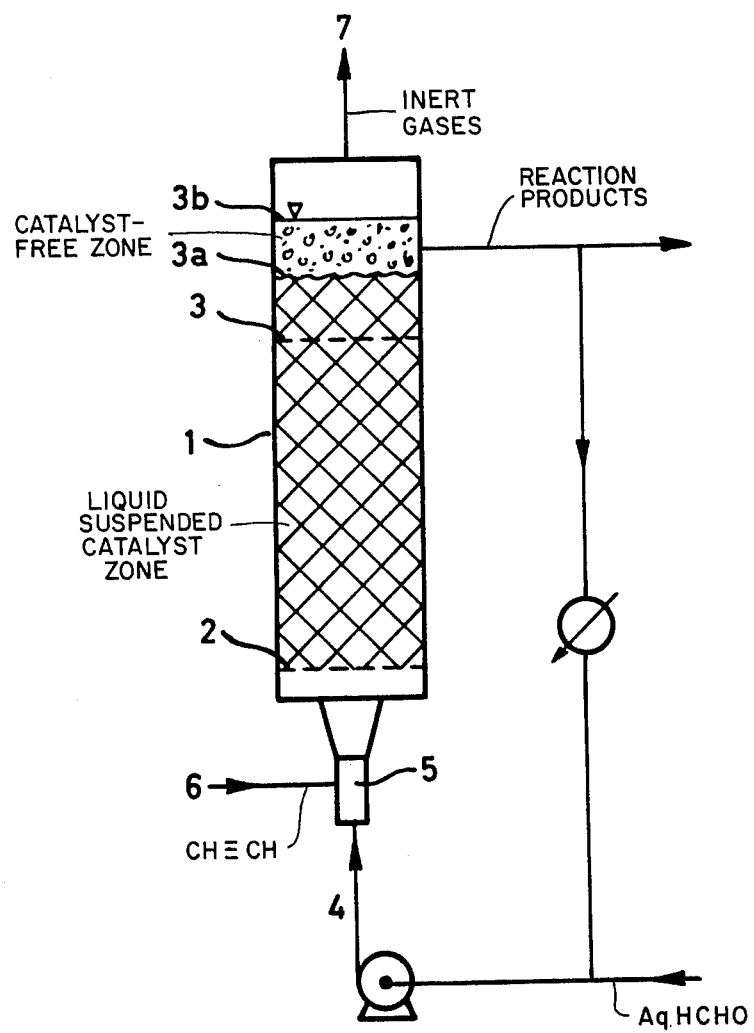

MANUFACTURE OF BUTYNEDIOL

This invention relates to a suspended catalyst promoted process for the production of butynediol from acetylene and formaldehyde.

Butynediol is manufactured industrially by reacting formaldehyde with acetylene in liquid phase, particularly aqueous phase, in the presence of a heavy metal acetylide catalyst.

Butynediol is a very valuable intermediate in the manufacture of butanediol, tetrahydrofuran, pyrrolidone and other products.

The conventional processes for the manufacture of butynediol are mostly operated under pressure. Pressures in the range of approximately 2 to 7 bars are common, and as a safety precaution the reactors must be designed to withstand 12 times the operating pressure.

Methods have also become known which operate under no substantial pressure. Such a process is revealed, for example, in German Published Application No. 1,906,051.

The processes are differentiated according to the arrangement of the catalyst in the reaction chamber, i.e. processes in which the catalyst is in the form of a fixed bed and processes in which the catalyst is in suspension, i.e. in a fine state of subdivision, in the liquid.

Processes involving a suspended catalyst have scarcely been adopted in industry, because the recovery of the pure, catalyst-free liquid for working up to butynediol presents difficulties.

It is an object of the invention to provide an industrial process in which the reaction of acetylene with formaldehyde is effected in liquid phase in contact with a catalyst suspended in said liquid phase. If such a process should succeed, it would have the advantage that the relatively large catalyst surface area would enable considerable reaction rates to be achieved and would consequently make it possible to do without the use of elevated acetylene pressures for achieving satisfactory reaction rates. Another advantage of a commercially useful process using suspended catalysts is that problems of overheating such as always occur in fixed beds of catalysts and render the catalyst or catalyst packing useless are overcome.

One proposal of this kind is made, for example, in Soviet Chemical Industry, pp. 885-887 (1968). This process is carried out in a reactor containing a relatively cocentrated pasty catalyst suspension having a solids content of up to 50%, the reacted liquid being withdrawn from the reaction chamber via a filter candle.

The use of a filter candle in a suspension-filled reaction chamber has of course its problems where an industrial process is concerned, since experience has shown that such filter candles must be frequently cleaned or replaced.

U.S. Pat. No. 2,987,465 proposes a hydrogenation process in which the required catalyst suspension is constantly agitated by means of a circulating liquid, which catalyst suspension does not fill the entire reaction chamber, but instead the catalyst is suspended in the liquid only in the lower part of the reaction chamber, whilst a substantially catalyst-free liquid zone is present above the catalyst, from which zone the liquid can be withdrawn. In this case, hydrogen is passed up through the liquid to effect hydrogenation and is withdrawn above the liquid. Experiments have shown that the passage of a gas in the form of bubbles through a catalyst-containing liquid zone makes it very difficult if not impossible to establish a catalyst-free liquid zone above the catalyst when the liquids concerned have relatively low viscosities.

We have now found that the manufacture of butynediol by the reaction of formaldehyde with acetylene in liquid phase in the presence of a heavy metal acetylide (supported) catalyst forming a suspension of solid particles in the liquid reaction mixture, the gaseous acetylene being fed up through the suspension, may be successfully carried out with the advantage of a high reaction rate and little tendency to develop faults when (for a given size and/or size distribution of the catalyst particles) the liquid is fed to the reaction chamber in known manner at such a rate that the catalyst suspension agitated by the liquid stream does not completely or not homogeneously fill the liquid zone but leaves a substantially catalyst-free liquid zone above the suspension and when the acetylene is fed at such a rate that it is substantially completely consumed on passing through the reaction chamber.

The success of this process is particularly surprising, since it is seen that a high reaction rate is obtained even when the acetylene is not provided in excess and, moreover, when the process is not carried out at elevated pressure.

The process may, of course, be carried out under elevated pressure, for example a pressure of up to 7 atmospheres, but the use of atmospheric pressure is perfectly adequate. As a safety precaution, i.e. in order to ensure that no air enters the reaction chamber via its outlet, it is in many cases advantageous, however, to use slightly increased pressure. The reaction temperature used should be in the usual range, i.e. from about 70° to 100° C and in particular at about 90° C.

Suitable heavy metal acetylide catalysts for use in the present invention are those already disclosed by Reppe (see for example "Chemie und Technik der Acetylendruckreaktionen", Verlag Chemie, Weinheim, 1951). Particularly suitable catalysts are those heavy metal acetylide catalysts, particularly copper(I) acetylide catalysts, which have been prepared by impregnating a support of appropriate particle size distribution with copper or heavy metal salt solutions followed by treatment with gaseous acetylene in the liquid phase.

For the purposes of the present invention it is advantageous to reduce the size of the particulate support to an appropriate particle size, e.g. ranging from 0.1 to 3 mm, and to impregnate the powdered supporting composition thus obtained with a heavy metal salt solution in the manner described followed by treatment with formaldehyde solution and conversion to the heavy metal acetylide with acetylene.

We prefer to use a catalyst which contains from about 10 to 15% of copper and from 2 to 5% of bismuth supported on silica gel, said percentages being based on the total weight of catalyst.

A preferred mode of operation of the process of the invention is illustrated by the accompanying drawing, which will now be described. The reaction chamber is formed by a tank 1 containing the catalyst in liquid suspension. In a quiescent state, the catalyst particles are retained by a sieve 2 and occupy a space of which the upper limit is indicated in the drawing by a broken line 3. The liquid above this line is free from catalyst. When liquid is passed into the reactor through line 4, the catalyst is unsettled and, when the liquid feed does not exceed an experimentally predetermined limit, the catalyst eventually occupies a zone of which the upper limit is indicated in the drawing by a wavy line 3a. Above this line there is a substantially catalyst-free liquid zone having the upper limit 3b.

The following method of feeding the acetylene to the reactor has proved successful. On its way to the reaction chamber, the liquid passes through a filter-pump-like injector arrangement 5, by means of which the available gas phase is sucked in through line 6 and thus finely distributed. The rate of gas flow can be adjusted by suitable control means in the gas feed line so that the gas is virtually completely consumed on passing through the reaction chamber in the form of fine bubbles. Complete consumption, however, is not desirable; neither is it possible, since commercial grade acetylene usually contains a certain proportion of inert gases, such as other hydrocarbons, e.g. saturated hydrocarbons, which accumulate in the exhaust stream and must be removed therefrom, as is also normally the case in prior art processes. However, the amount of gas passing through the catalyst-free liquid zone to the exhaust line 7 is so small that no catalyst particles are entrained from the lower zone containing suspended catalyst to the upper, catalyst-free zone.

The above remarks mean that, in the case of a reactor of substantially cylindrical construction, the catalyst suspension originally placed on the sieve 2 is diluted when the liquid feed is commenced to a volume which is at least 5% and in general from about 10 to 25% greater than its original volume or, if the reaction chamber is not cylindrical, to a height which is a corresponding fraction greater than its original height.

A suitable liquid medium is usually water, but in certain embodiments an alcohol or similar liquid such as tetrahydrofuran may be suitable.

when selecting a suitable catalyst particle size it is usually only necessary to ensure that the density of the catalyst particles does not differ unduly from the density of the liquid medium in which they are to be suspended. The macroscopic density of heavy metal acetylide catalysts supported on silica gel is found to be about 1.1 g/cm$^3$ and is highly suitable for use in the present process. Where an aqueous system is used, a liquid throughput of from about 10 to 60 m$^3$ per m$^2$ per hour is necessary and adequate under these conditions in order to give the zones forming a feature of the invention. The reactor which is shown in the accompanying drawing as a cylinder for the sake of simplicity, may of course have any other shape, such as that of a funnel or of a cylindrical vessel having a funnel-shaped base, or the upper part of the reaction chamber may have a different diameter from the middle and lower parts. The fact that liquid is fed into the reactor from the bottom obviously requires the removal of liquid from the top if a constant level of liquid is to be maintained. For practical reasons, a portion of the liquid fed to the bottom is a stream of liquid removed from the liquid withdrawn at the top, only a portion of said latter liquid being taken for the recovery of butynediol. It is of course equally possible to remove liquid from the catalyst-containing part of the reaction chamber for recycling to the bottom of the reactor for agitating the catalyst, but it is generally preferable, on account of a certain proneness of the catalyst particles to size reduction due to mechanical damage, to use a process in which the liquid fed to the bottom contains no suspended catalyst.

The above-described process is particularly suitable for continuous operation and, when suitable apparatus is used, it can be operated in such a manner that the catalyst may be replaced over long periods of time without interrupting the reaction.

The invention is described below with reference to an Example, in which the high space-time yields are particularly noteworthy. In this Example the parts are by weight unless otherwise stated.

EXAMPLE

Using an apparatus corresponding to the above description and the accompanying drawing, which has a cylindrical reaction chamber having a diameter of 10 cm and a height of 50 cm and filled with 2.5 dm$^3$ of catalyst particles having an average diameter of 1 mm and a particle size distribution of from 0.1 to 1.2 mm, an aqueous formaldehyde solution is reacted with acetylene at atmospheric pressure. The catalyst contains 12% of copper in the form of copper acetylide and 3% of bismuth supported on silicon dioxide. The particles are unsettled by a liquid stream of 0.35 m$^3$/hr pumped up through the reaction chamber, the catalyst bed being expanded thereby by about 20% compared with the quiescent state.

At a continuous feed of 0.5 kg/hr of 30% aqueous formaldehyde solution, a reaction temperature of 90° C and a pH of 4.6 maintained constant by the addition of caustic soda, the reaction product has a formaldehyde content of 10%, a butynediol content of 24%, a propargyl alcohol content of 0.4% and a non-distillable residue of 0.5%. This is equivalent to a space-time yield of 1.3 kg of butynediol per liter of catalyst per day, and this remains constant over a period of several months.

We claim:

1. A continuous process for the manufacture of butynediol which comprises reacting acetylene and formaldehyde in a liquid medium containing particles of a metal acetylide on a catalyst support, said particles being suspended in the liquid medium, said particles having diameters in the range of 0.1 to 3 mm. and a macroscopic density of about 1.1 g/cm$^3$, withdrawing liquid reaction product from the upper portion of said chamber, said liquid reaction product in said portion being substantially free of suspended catalyst particles, recycling a portion of said reaction product to the lower portion of said reaction chamber and supplying said recycled liquid reaction product into the lower portion of said chamber in admixture with fresh aqueous formaldehyde solution to form said liquid medium in said chamber, flowing said liquid medium upwardly through said reaction chamber at a liquid medium throughput of about 10 to 60 m$^3$ per m$^2$ per hour and provide in the reaction chamber a liquid medium velocity sufficient to maintain said catalyst particles in a suspended state in the upwardly flowing liquid medium with the upper zone of said liquid medium being substantially free of catalyst particles, said liquid product being withdrawn from said substantially catalyst-free upper zone, and feeding gaseous acetylene into the lower portion of said chamber with the gaseous acetylene finely distributed in the liquid medium at a rate at which the acetylene is virtually completely consumed in the liquid medium in said chamber.

2. A process as claimed in claim 1 wherein the support for said catalyst is silica gel.

3. A process as claimed in claim 1 wherein the volume of liquid medium containing the suspended catalyst particles is at least 5% greater than the volume of the catalyst particles when they are not suspended by said liquid medium.

4. A process as claimed in claim 1 wherein said gaseous acetylene is fed to the liquid medium in a substantially non-pressurized state.

* * * * *